United States Patent [19]

Austin

[11] Patent Number: Plant 7,215

[45] Date of Patent: Apr. 10, 1990

[54] ROSE PLANT 'AUSCOT'

[75] Inventor: David C. H. Austin, Albrighton, England

[73] Assignee: David Austin Roses, Albrighton, England

[21] Appl. No.: 259,281

[22] Filed: Oct. 18, 1988

[51] Int. Cl.[4] ..... A01H 5/00

[52] U.S. Cl. ..... Plt./1

[58] Field of Search ..... Plt./1

*Primary Examiner*—James R. Feyrer

*Attorney, Agent, or Firm*—Ladas & Parry

[57] ABSTRACT

A new variety of rose plant of the shrub class distinctive in its character by its fully double, apricot yellow flowers, with abundant, continual blooming and the unusual blend of coloring and shaping of the flower.

1 Drawing Sheet

BACKGROUND OF THE INVENTION

The present invention relates to a new and distinct variety of shrub rose, a seedling resulting from a definite effort to produce an improvement in this class of roses.

SUMMARY OF THE INVENTION

Primary features of this new variety which connote a distinctive advance over existing types are the vigorous abundant and continual blooming taken with the perfection of the fully double flowers of an old-fashioned type more particularly apparent in the accompanying illustration of a specimen thereof.

BRIEF DESCRIPTION OF THE DRAWING

The drawing depicts, from side view, stems, foliage, flower buds and flowers in various stages of development.

DETAILED BOTANICAL DESCRIPTION

The following is a detailed description of the new variety, colour terminology being in accordance with the "Methuen Handbook of Colour" published by Eyre Methuen Ltd. (1963).

Variety denomination (in accordance with the UPOV Convention): Auscot (Trade name Abraham Derby).

Type: Hardy; bush; outdoor; seedling; for cut flowers and garden decoration.

Class: Shrub.

Propagation: holds its distinguishing characteristics through succeeding propagations by budding.

The rose plant was grown at Albrighton, Nr. Wolverhampton, England and was derived as follows:

Female parent (seed parent): Aloha.

Male parent (pollen parent): Yellow Cushion.

The operation of the artificial pollination is therefore expressed by the following (Aloha×Yellow Cushion).

The following observations are made of specimens grown outdoors in England.

Plant Description

Plant:

*Height.*—135–165 cm.

*Habit.*—Tall, strong, arching.

Branches:

*Colour.*—Young stems: Deep Green 29 E8, tinged with red on one side. Adult wood: Deep Green 30 E8.

Leaves:

*Stipules.*—Mid Green — broad. Finely dentate at edges, sometimes glandular hairy. 2 wings.

*Petiol.*—Upper side — flat with raised edge — flattish — few glandular hairs. Under side — Mid Green — very occasional small thorns.

*Folioles.*—5 with 3 at base of flower. Shape — ovate, slightly accuminate. Serration — dentate. Texture — leathery.

*General effect.*—Dense, glossy foliage.

*Colour.*—Young foliage — Upper side — Deep Green 30 E8, tinged with Red. Under side — Medium Brown, 10 F6, turning Green. Adult foliage — Upper Side — Dark Green 30 F8. Under Side — Medium Green 28 E6.

Hips and seed: This variety does not produce seed in normal garden conditions, but only when cross-pollinated.

Inflorescence

Number of flowers: From 1 to 4 but generally 3.

Peduncle: Thick light Green, rigid, light red glandular aciculas, with occasional small prickles. The thorns on the main stem are medium thorny and of average size. The colour ranges from 10D 8 when young to 9D 6 when mature.

*Length.*—10 cm on average.

Sepals: Upper side: Light Green — moderately finely hairy. Under side: Medium to Light Green, Glabrous edges with occasional wings — finely and glandular hairy.

Bud:

*Shape.*—Flask shaped.

*Length.*—3.5 cm.

*Size.*—Large.

*Colour.*—When opening. Upper side: Deep Red 11 D7. Under side: Deep Yellow turning to Light Green 1 C8 at base merging into deep red 11 D7 at tip.

Flower:

*Shape.*—Large cup shaped, quartered.

*Diameter:* 10 cm on average.

*Colour:* When opening. Upper side: Yellow 3 A8 at base, merging into very deep pink 9 B8. Under side: Yellow 3 A8 at base, merging into light red 10 B6. When blooming: Upper side: Yellow 4

A8, merging into Light Red 10 A4. Under Side: Reddish Yellow 4 A7 at base, merging into Pale Red 9 A3 at very outside. When finished blooming: Upper Side: Yellow 4 A8 merging into Medium Red 10 B4. Under Side: Reddish Yellow 4 A7 turning to Pale Red 9 A3.

*Fragrance.*—Very strong — fruit-like.

*Lasting quality.*—Very good.

Petals:

*Shape.*—Ovate with a truncated base.

*Texture.*—Silky tough.

*Number.*—70 on average.

*Cleaning.*—Good.

Reproductive Organs

Stamens:

*Number.*—138.

*Anthers.*—Butter yellow.

*Filaments.*—Yellow to Red. Variable length.

Pistils:

*Number.*—44 on average.

*Stigmas.*—Yellow.

*Styles.*—Greenish Yellow — very hairy. Receptacle — Shallow cup — Bright Yellow. Raised rim — Light Green.

The development:

*Vegetation.*—Vigorous.

*Blooming.*—Abundant and continual.

*Aptitude to bear fruits.*—Normal.

*Resistance to frost.*—Good.

*Resistance to diseases.*—Good.

I claim:

1. A new and distinct variety of rose plant of the shrub class, characterised as to novelty by its fully double, apricot-yellow flowers with abundant and continual blooming the unusual blend of colouring and shaping of the flower being substantially as shown and described.

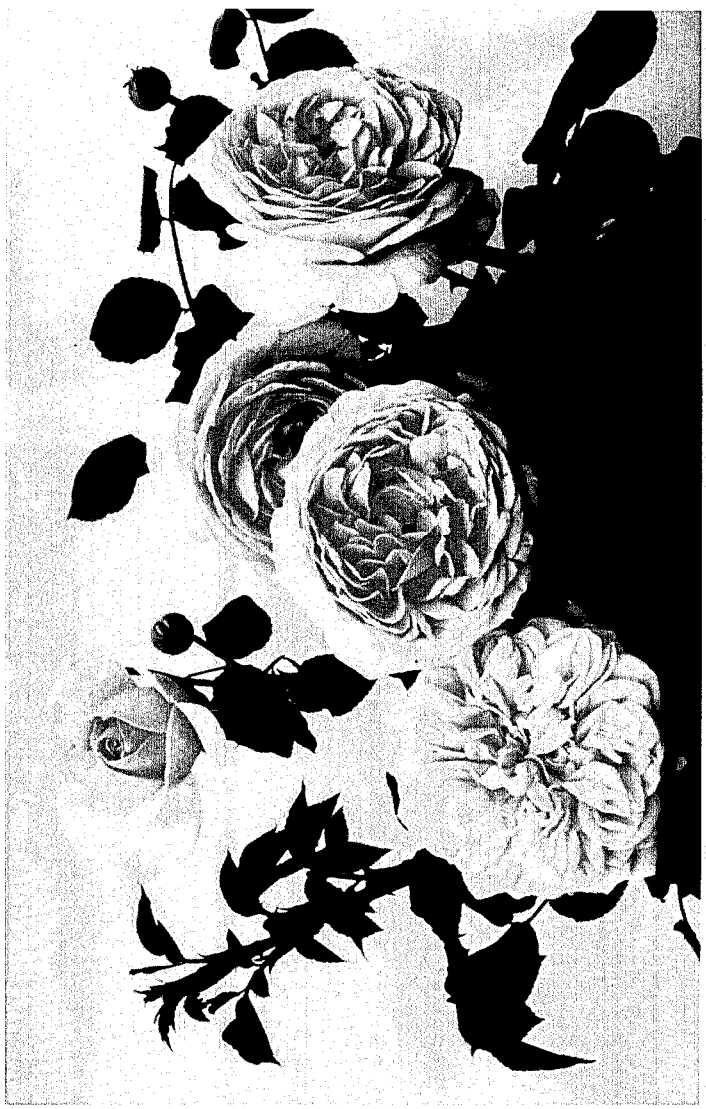

* * * * *